(12) United States Patent
Govari et al.

(10) Patent No.: US 12,201,786 B2
(45) Date of Patent: Jan. 21, 2025

(54) MEASUREMENT OF DISTAL END DIMENSION OF CATHETERS USING MAGNETIC FIELDS

(71) Applicant: Biosense Webster (Israel) Ltd., Yokneam (IL)

(72) Inventors: Assaf Govari, Haifa (IL); Vadim Gliner, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 220 days.

(21) Appl. No.: 17/125,879

(22) Filed: Dec. 17, 2020

(65) Prior Publication Data

US 2022/0193370 A1 Jun. 23, 2022

(51) Int. Cl.
*A61M 25/01* (2006.01)
*A61B 18/00* (2006.01)
*A61B 18/14* (2006.01)

(52) U.S. Cl.
CPC ..... *A61M 25/0127* (2013.01); *A61B 18/1492* (2013.01); *A61B 2018/00577* (2013.01)

(58) Field of Classification Search
CPC .... A61M 25/0127; A61B 5/287; A61B 5/367; A61B 5/6858; A61B 5/062; A61B 5/283; A61B 18/12; A61B 18/14; A61B 18/1492; A61B 2018/00577; A61B 2018/00404; A61B 2562/0223
See application file for complete search history.

(56) References Cited

U.S. PATENT DOCUMENTS

| 4,699,147 A | 10/1987 | Chilson et al. |
| 4,940,064 A | 7/1990 | Desai |
| 5,215,103 A | 6/1993 | Desai |

(Continued)

FOREIGN PATENT DOCUMENTS

| CN | 111248993 A | 6/2020 |
| CN | 111248996 A | 6/2020 |

(Continued)

OTHER PUBLICATIONS

Translation of CN 111388085 A (Year: 2020).*
Extended European Search Report dated May 4, 2022, from corresponding European Application No. 21215040.3.

*Primary Examiner* — Pascal M Bui Pho
*Assistant Examiner* — Neshat Baset

(57) ABSTRACT

In one embodiment, a system includes generator coils to generate respective magnetic fields, a catheter including a distal end, which includes magnetic coil sensors to output electrical signals based on detection of the respective magnetic fields, and processing circuitry to receive the electrical signals from the magnetic coil sensors, select at least one of magnetic fields having a magnetic field gradient as a function of at least one of the received electrical signals, compute a difference between magnetic field magnitudes of the at least one selected magnetic field detected by the first magnetic coil sensor and the second magnetic coil sensor as a function of the electrical signals, and compute a dimension of the distal end, based on the difference between the magnetic field magnitudes of the at least one selected magnetic field and the magnetic field gradient of the at least one selected magnetic field.

21 Claims, 4 Drawing Sheets

(56) References Cited

U.S. PATENT DOCUMENTS

| | | |
|---|---|---|
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,443,489 A | 8/1995 | Ben-Haim |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,558,091 A | 9/1996 | Acker et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,172,499 B1 | 1/2001 | Ashe |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,788,967 B2 | 9/2004 | Ben-Haim et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |

(56) References Cited

U.S. PATENT DOCUMENTS

| | | | |
|---|---|---|---|
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1* | 1/2006 | Fuimaono .............. A61B 5/283 600/509 |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0172455 A1* | 6/2017 | Pressman .............. A61B 5/287 |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1* | 6/2018 | Govari .............. A61B 18/1492 |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1* | 12/2018 | Bar-Tal .............. A61B 5/287 |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |

(56) References Cited

U.S. PATENT DOCUMENTS

| | | |
|---|---|---|
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0226046 A1* | 7/2022 | Mariappan ............. A61B 5/063 |

FOREIGN PATENT DOCUMENTS

| | | | |
|---|---|---|---|
| CN | 111388085 A * | 7/2020 | ............. A61B 18/12 |
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 2578173 B1 | 6/2017 | |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3972510 A1 | 3/2022 | |
| WO | 9421167 A1 | 9/1994 | |
| WO | 9421169 A1 | 9/1994 | |
| WO | 1996/005768 A1 | 2/1996 | |
| WO | 9625095 A1 | 8/1996 | |
| WO | 9634560 A1 | 11/1996 | |
| WO | 0182814 B1 | 5/2002 | |
| WO | 2004087249 A2 | 10/2004 | |
| WO | 2012100185 A2 | 7/2012 | |
| WO | 2013052852 A1 | 4/2013 | |
| WO | 2013162884 A1 | 10/2013 | |
| WO | 2013173917 A1 | 11/2013 | |
| WO | 2013176881 A1 | 11/2013 | |
| WO | 2014176205 A1 | 10/2014 | |
| WO | 2016019760 A1 | 2/2016 | |
| WO | 2016044687 A1 | 3/2016 | |
| WO | 2018111600 A1 | 6/2018 | |
| WO | 2018191149 A1 | 10/2018 | |
| WO | 2019084442 A1 | 5/2019 | |
| WO | 2019143960 A1 | 7/2019 | |
| WO | 2020026217 A1 | 2/2020 | |
| WO | 2020206328 A1 | 10/2020 | |

* cited by examiner

MEASUREMENT OF DISTAL END DIMENSION OF CATHETERS USING MAGNETIC FIELDS

FIELD OF THE INVENTION

The present invention relates to medical systems, and in particular, but not exclusively, to catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the tip electrode(s) of the ablating catheter, and the reference electrode, flowing through the media between the electrodes it, i.e., blood and tissue. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

SUMMARY

There is provided in accordance with an embodiment of the present disclosure, a medical system including generator coils configured to generate respective magnetic fields having respective different frequencies in a region of a body part of a living subject, a catheter configured to be inserted into the body part of the living subject, and including a distal end, which includes magnetic coil sensors configured to output electrical signals as a function of detecting the respective magnetic fields, and including a first magnetic coil sensor having a first axis and a second magnetic coil sensor having a second axis, the magnetic coil sensors being disposed on the distal end with the first axis being substantially parallel with the second axis, and processing circuitry configured to receive the electrical signals from the magnetic coil sensors, select at least one of the magnetic fields having a magnetic field gradient as a function of at least one of the received electrical signals, compute a difference between magnetic field magnitudes of the at least one selected magnetic field detected by the first magnetic coil sensor and the second magnetic coil sensor based on the received electrical signals, and compute a dimension of the distal end, which is a function of a distance between the magnetic coil sensors, based on the computed difference between the magnetic field magnitudes of the at least one selected magnetic field and the magnetic field gradient of the at least one selected magnetic field.

Further in accordance with an embodiment of the present disclosure the computed dimension is the distance between the magnetic coil sensors.

Still further in accordance with an embodiment of the present disclosure the computed dimension is a dimension of a shape of the distal end of the catheter.

Additionally, in accordance with an embodiment of the present disclosure the processing circuitry is configured to compute the dimension of the distal end based on the computed difference between the magnetic field magnitudes of the at least one selected magnetic field divided by the magnetic field gradient of the at least one selected magnetic field.

Moreover, in accordance with an embodiment of the present disclosure the at least one selected magnetic field includes one of the magnetic fields having a highest magnetic field gradient of the magnetic fields, and the processing circuitry is configured to compute the dimension of the distal end based on the computed difference between the magnetic field magnitudes of the at least one selected magnetic field and the highest magnetic field gradient.

Further in accordance with an embodiment of the present disclosure the catheter has a longitudinal axis, and the distal end of the catheter includes an expandable distal end assembly, the magnetic field sensors being configured to move with respect to each other along the longitudinal axis of the catheter as the expandable distal end assembly is expanded and collapsed, when the expandable distal end assembly is collapsed the distance between the magnetic coil sensors increases, and when the expandable distal end assembly is deployed the distance between the magnetic coil sensors decreases.

Still further in accordance with an embodiment of the present disclosure the first axis, second axis, and the longitudinal axis are substantially coaxial.

Additionally, in accordance with an embodiment of the present disclosure the expandable distal end assembly is a basket distal end assembly including a plurality of flexible strips and electrodes disposed on the flexible strips.

Moreover, in accordance with an embodiment of the present disclosure, the system includes a display, and wherein the processing circuitry is configured to find a shape of the distal end assembly based on at least the computed dimension, and render to the display a representation of the distal end assembly based on the found shape of the distal end assembly.

Further in accordance with an embodiment of the present disclosure the computed dimension is the distance between the magnetic coil sensors.

Still further in accordance with an embodiment of the present disclosure the processing circuitry is configured to compute a relative orientation between the first axis of the first magnetic coil sensor and the second axis of the second magnetic coil sensor, and estimate a shape of the distal end assembly based on the computed relative orientation.

There is also provided in accordance with another embodiment of the present disclosure, a medical method, including generating magnetic fields having respective different frequencies in a region of a body part of a living subject, inserting a catheter into the body part of the living subject, magnetic coil sensors with substantially parallel axes disposed on a distal end of the catheter outputting electrical signals as a function of detecting the respective ones of the magnetic fields, and receiving the electrical signals from the magnetic coil sensors, selecting at least one of the magnetic fields having a magnetic field gradient based on at least one of the received electrical signals, computing a difference between magnetic field magnitudes of the at least one selected magnetic field detected by a first one of the magnetic coil sensors and a second one of the magnetic coil sensors based on the received electrical signals, and computing a dimension of the distal end, which is a function of a distance between the magnetic coil sensors, based on the computed difference between the magnetic field magnitudes of the at least one selected magnetic field and the magnetic field gradient of the at least one selected magnetic field.

Additionally, in accordance with an embodiment of the present disclosure the computed dimension is the distance between the magnetic coil sensors.

Moreover, in accordance with an embodiment of the present disclosure the computed dimension is a dimension of a shape of the distal end of the catheter.

Further in accordance with an embodiment of the present disclosure the computing the dimension includes computing the dimension of the distal end based on the computed difference between the magnetic field magnitudes of the at least one selected magnetic field divided by the magnetic field gradient of the at least one selected magnetic field.

Still further in accordance with an embodiment of the present disclosure the at least one selected magnetic field includes one of the magnetic fields having a highest magnetic field gradient of the magnetic fields, and the computing the dimension includes computing the dimension of the distal end based on the computed difference between the magnetic field magnitudes of the at least one selected magnetic field and the highest magnetic field gradient.

Additionally, in accordance with an embodiment of the present disclosure, the method includes moving the magnetic field sensors with respect to each other along a longitudinal axis of the catheter as an expandable distal end assembly of the catheter is expanded and collapsed.

Moreover, in accordance with an embodiment of the present disclosure the first axis, second axis, and the longitudinal axis are substantially coaxial.

Further in accordance with an embodiment of the present disclosure, the method includes finding a shape of the distal end assembly based on at least the computed dimension, and rendering to a display a representation of the distal end assembly based on the found shape of the distal end assembly.

Still further in accordance with an embodiment of the present disclosure the computed dimension is the distance between the magnetic coil sensors.

Additionally, in accordance with an embodiment of the present disclosure, the method includes computing a relative orientation between the first axis of the first magnetic coil sensor and the second axis of the second magnetic coil sensor, and estimating a shape of the distal end assembly based on the computed relative orientation.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
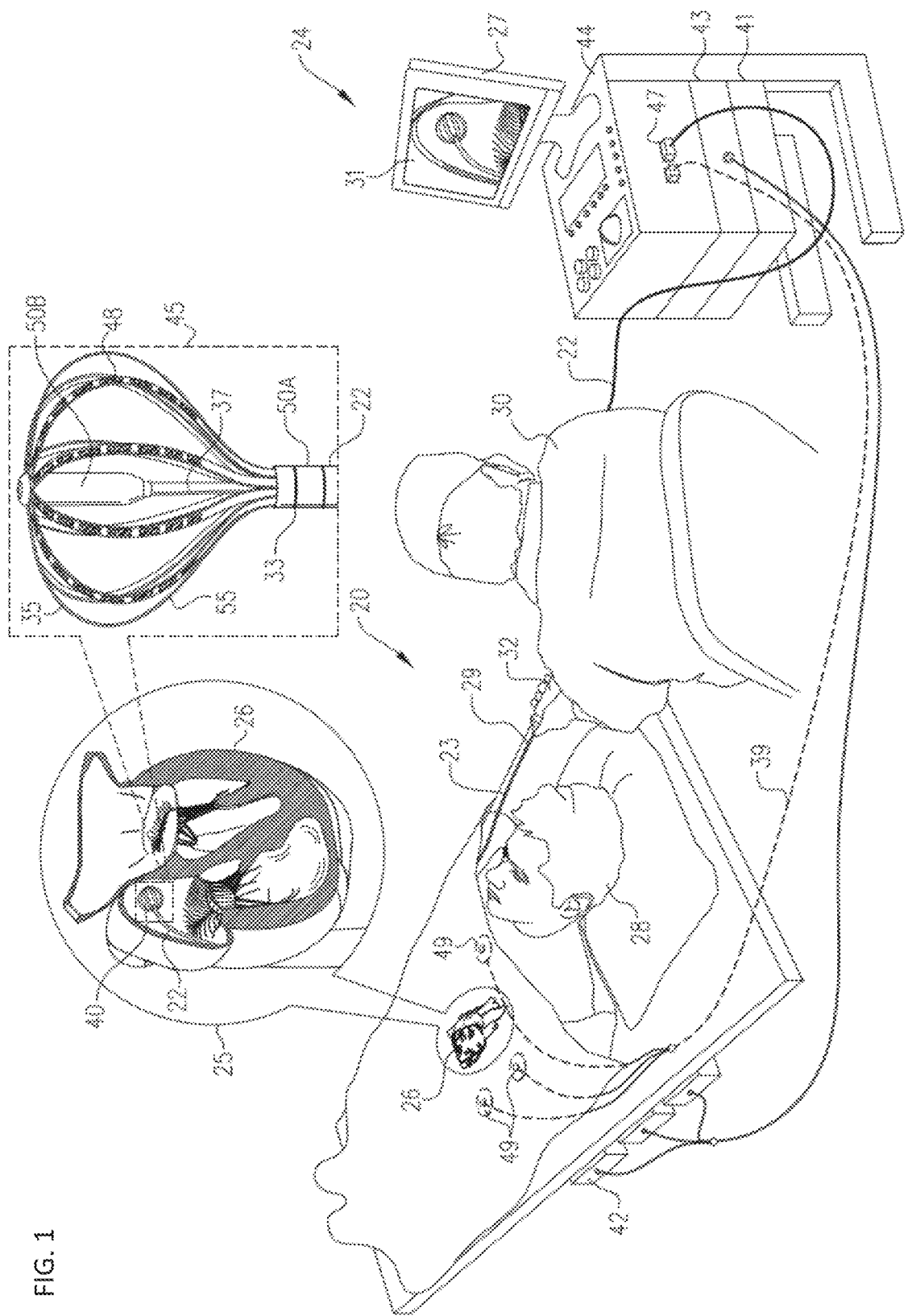
FIG. 1 is a schematic, pictorial illustration of a system for electro-anatomical mapping comprising a catheter, in accordance with an embodiment of the present invention.

The Carto®3 system (produced by Biosense Webster, Inc., Irvine, California) applies Advanced Catheter Location (ACL) hybrid position-tracking technology. In ACL technology, distribution of measured currents associated with probe electrodes on a catheter are correlated with a current-to-position matrix (CPM), which maps the current distribution to a position of the catheter that was previously acquired from magnetic location-calibrated position signals. The ACL technology enables locating and visualizing a catheter (even a catheter which does not have a magnetic field sensor), but only in the volume(s) where the CPM has been computed, using a catheter with a magnetic coil sensor. A prerequisite for building the CPM is to insert a magnetic-field sensor-equipped catheter into a body and move the catheter in a volume of the body, in order to compute the CPM for that volume.

Additionally, ACL technology may be used to track a basket catheter which has electrodes on the basket. However, ACL technology, which measures currents or impedances, may not provide high enough accuracy in some situations.

One solution is to use signals from magnetic sensors disposed on a catheter to compute the elongation of an expandable distal end assembly (such as a basket distal end assembly or a balloon distal end assembly) based on a distance between the magnetic sensors. The magnetic sensors can be placed on the catheter in such a manner that the distance between the sensors provides an indication of the elongation, and therefore the shape, of the distal end assembly. Magnetic sensors generally provide a more accurate position than using ACL. Nevertheless, the locations measured by the magnetic sensors are subject to errors, of the order of millimeters (e.g., 2 or 3 mm) and in some applications even these errors may be too large. For example, for a small basket catheter the distance between the magnetic sensors may change by about 10 or 15 millimeters between the basket being collapsed and the basket being deployed. Therefore, an error of 3 mm may be considered a large error. Errors may be reduced by using a Dual-Axis Sensor (DAS) or a Triple-Axis Sensor (TAS), which generally provide more accurate position measurements. However, in many applications, the catheter may not be able to accommodate two DASs or TASs or even one DAS or TAS. Details of magnetic location sensing are provided in commonly owned U.S. Pat. Nos. 5,391,199; 5,443,489, 5,558,091; 6,172,499; 6,690963; 6,788,967; and 6,892,091, which are hereby incorporated by reference with a copy provided in the Appendix.

Embodiments of the present invention provide a system and method which accurately compute a dimension of a distal end (e.g., an expandable distal end assembly such as a basket or balloon distal end assembly) of a catheter using magnetic-based tracking technology based on two magnetic coil sensors and magnetic field generators that generate respective alternating magnetic fields (of different frequencies) for detection by the sensors. The magnetic fields detected by the sensors are indicative of the position of the sensors within a given coordinate space.

The accuracy of the computation is based on two factors including the positioning of the two magnetic coil sensors and an accurate error-canceling computational method.

The magnetic coil sensors are placed along a longitudinal axis of the distal end of the catheter so that the axes of the two sensors are substantially parallel, and in some embodiments the two sensors are placed to be substantially coaxial with the longitudinal axis. In this way, both sensors sense the different alternating magnetic fields in a similar way (e.g., with respect to magnetic field gradients) so that in the computation described in more detail below one of the alternating magnetic fields may be used for both sensors and error-canceling between the two sensors may take effect. The term "substantially parallel", as used in the specification and claims, is defined as parallel within a tolerance of 10 degrees. However, the closer the axes of the two sensors are to being exactly parallel, the computations performed based on the output of the sensors will be more accurate. The term "substantially coaxial", as used in the specification and claims, is defined as the axes of the sensors being within 10 degrees of the longitudinal axis and the region between the windings of the sensors intersecting the longitudinal axis.

The error-canceling computation method includes computing respective magnetic field gradients of the respective magnetic fields (in a direction parallel to the axes of the sensors) which is detected at the distal end (e.g., at one or more of the sensors). The term "magnetic field gradient", as used in the specification and claims, is defined as the change of a magnetic field over distance in a particular direction. In some embodiments, an approximate position of one or more of the magnetic field sensors may be computed using any suitable method and then based on a known function of the different magnetic fields over three-dimensional (3D) space, the magnetic field gradients at the distal end (in a direction parallel to the axes of the sensors) may be found for each of the magnetic fields.

One of the magnetic fields is selected (e.g., the magnetic field having the highest magnetic field gradient). In some embodiments, a subset of the magnetic fields is selected (e.g., having the highest magnetic field gradients) and an average magnetic field gradient of the selected magnetic fields is computed.

A difference between magnetic field magnitudes of the selected magnetic field detected by the sensors is computed. When a subset of magnetic fields is selected, an average difference between magnetic field magnitudes of the selected magnetic fields detected by the sensors is computed.

The distance between the sensors may then be computed based on the (average) magnetic field gradient of the selected magnetic field(s) and the (average) difference between the magnetic field magnitudes of the selected magnetic field(s). In some embodiments, the distance may be computed based on dividing the (average) difference between the magnetic field magnitudes of the selected magnetic field(s) by the (average) magnetic field gradient of the selected magnetic field(s). Another dimension of the distal end assembly may be computed from the computed distance between the sensors. The distance and/or the dimension may then be used to find a shape of the distal end assembly so that a representation of the distal end assembly may be rendered to a display.

System Description

Reference is now made to FIG. 1, which is a schematic, pictorial illustration of a catheter tracking system 20, in accordance with an embodiment of the present invention. The system 20 includes a catheter 40 configured to be inserted into a body part of a living subject (e.g., a patient 28). A physician 30 navigates the catheter 40 (for example, a basket catheter produced by Biosense Webster, Inc. of Irvine, CA, USA), seen in detail in inset 45, to a target location in a heart 26 of the patient 28, by manipulating a deflectable segment of an insertion tube 22 of the catheter 40, using a manipulator 32 near a proximal end 29 of the insertion tube 22, and/or deflection from a sheath 23. In the pictured embodiment, physician 30 uses catheter 40 to perform electro-anatomical mapping of a cardiac chamber.

The catheter 40 includes a distal end 33. The distal end 33 of the catheter 40 includes an assembly 35 (e.g., a basket assembly as shown in FIG. 1 or a balloon assembly) on which multiple electrodes 48 (only some labeled for the sake of simplicity) are disposed. The assembly 35 is disposed distally to the insertion tube 22 and may be connected to the insertion tube 22 via a coupling member of the insertion tube 22 at the distal end 33. The coupling member of the insertion tube 22 may be formed as an integral part of the rest of the insertion tube 22 or as a separate element which connects with the rest of the insertion tube 22.

The assembly 35 further comprises multiple flexible strips 55 (only two labeled for the sake of simplicity), to each of which are coupled the electrodes 48. The assembly 35 may include any suitable number of electrodes 48. In some embodiments, the assembly 35 may include ten flexible strips 55 and 120 electrodes, with twelve electrodes disposed on each flexible strip 55.

The catheter 40 includes a pusher 37. The pusher 37 is typically a tube that is disposed in a lumen of the insertion tube 22 and spans from the proximal end 29 to the distal end 33 of the insertion tube 22. A distal end of the pusher 37 is connected to first ends of the flexible strips 55, typically via a coupling member of the pusher 37. The coupling member of the pusher 37 may be formed as an integral part of the rest of the pusher 37 or as a separate element which connects with the rest of the pusher 37. The distal end of the insertion tube 22 is connected to second ends of the flexible strips 55, typically via the coupling member of the distal end 33. The pusher 37 is generally controlled via the manipulator 32 to deploy the assembly 35 and change an ellipticity of the assembly 35 according to the longitudinal displacement of the pusher 37 with respect to the insertion tube 22.

The actual basket assembly 35 structure may vary. For example, flexible strips 55 may be made of a printed circuit board (PCB), or of a shape-memory alloy.

Embodiments described herein refer mainly to a basket distal-end assembly 35, purely by way of example. In alternative embodiments, the disclosed techniques can be used with a catheter having a balloon-based distal-end assembly or of any other suitable type of distal-end assembly.

Catheter 40 is inserted in a folded configuration, through sheath 23, and only after the catheter 40 exits sheath 23 is catheter 40 able to change shape by retracting pusher 37. By containing catheter 40 in a folded configuration, sheath 23 also serves to minimize vascular trauma on its way to the target location.

The distal end 33 of the catheter 40 comprises magnetic coil sensors 50A and 50B. The magnetic coil sensor 50A is shown in inset 45 at the distal edge of insertion tube 22 (i.e., at the proximal edge of basket assembly 35). The sensor 50A may be a Single-Axis Sensor (SAS), or a DAS or a TAS. Similarly, the sensor 50B may be a SAS, DAS, or TAS. Magnetic coil sensors 50A and 50B and electrodes 48 are connected by wires running through insertion tube 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between sensors 50A and 50B as described in more detail with reference to FIGS. 2B and 3. Patient 28 is placed in a magnetic field generated by a pad containing multiple magnetic field generator coils 42, which are driven by a unit 43. The magnetic field generator coils 42 are configured to generate respective alternating magnetic fields, having respective different frequencies, into a region where a body-part (e.g., the heart 26) of a living subject (e.g., the patient 28) is located. The magnetic coil sensors 50A and 50B are configured to output electrical signals as a function of detecting the respective magnetic fields. For example, if there are nine magnetic field generator coils 42 generating nine respective different alternating magnetic fields with nine respective different frequencies, the electrical signals output by the magnetic coil sensors 50 will include components of the nine different frequency alternating magnetic fields. The magnitude of each of the magnetic fields varies with distance from the respective magnetic field generator coils 42 such that the location of the magnetic coil sensors 50 may be determined from the magnetic fields sensed by the magnetic coil sensors 50. Therefore, the transmitted alternating magnetic fields generate the electrical signals in sensors 50A and 50B, so that the electrical signals are indicative of position and orientation of the magnetic coil sensors 50. The magnetic coil sensors 50A and 50B are described in more detail with reference to FIG. 2B.

The generated signals are transmitted to console 24 and become corresponding electrical inputs to processing circuitry 41. The processing circuitry 41 may use the signals to compute: the elongation of the basket assembly 35, in order to estimate basket ellipticity and elongation/retraction state from the calculated distance between sensors 50A and 50B, described in more detail below with reference to FIGS. 2B and 3; and compute a relative orientation between the axes of the sensors 50A and 50B to estimate a shape of the expandable distal end assembly 35 (e.g., a basket shape) based on the relative orientation, as described in more detail below.

The bow of the flexible strips 55 and/or the positions of the electrodes 48 (or other features) on the flexible strips 55 with respect to a fixed point on the catheter 44 (such as the distal tip of the insertion tube 22) may be measured for various distances between the magnetic sensors 50A, 50B and for various relative orientation angles between the magnetic sensors 50A, 50B. For example, the positions of the electrodes 48 with respect to the fixed point on the catheter 40 may be measured for every 0.2 mm movement of the pusher 37 with respect to the insertion tube 22 and for every 1 degree of relative orientation between the magnetic sensors 50A, 50B (up to a maximum sideways movement of the assembly 35). At each different distance/relative-orientation combination, the computed distance and computed relative orientation angle between the magnetic sensors 50A, 50B is recorded along with the position data of the electrodes 48. This data may then be used to estimate the bow of the flexible strips 55 and/or the positions of the electrodes 48 (or other features) on the flexible strips 55 with respect to a fixed point on the catheter 40 (such as the distal tip of the insertion tube 22) based on the computed distance and relative orientation angle between the magnetic sensors 50A, 50B.

Additionally, or alternatively, the bow of the flexible strips 55 may be estimated based on the following assumptions: (a) each of the flexible strips 55 is of a fixed and known length; (b) each of the flexible strips 55 is connected to the pusher 37 via a coupler, with the distal ends of the flexible strips 55 being substantially perpendicular (within an error of plus or minus 10 degrees) to the longitudinal axis 58; (c) each of the flexible strips 55 is connected to the insertion tube 22 via a coupler, which couples the proximal ends of the flexible strips 55 to the insertion tube 22, substantially parallel (within an error of plus or minus 10 degrees) to the longitudinal axis 58 of the insertion tube 22. Based on the above assumptions (a)-(c), and the computed positions of the couplers based on the computed positions of the magnetic sensors 50A, 50B, the bow of each of the flexible strips 55 may be computed using a third-degree polynomial. In some embodiments, the bow of the flexible strips 55 and/or the positions of the electrodes 48 (or other features) on the flexible strips 55 with respect to a fixed point on the catheter 40 (such as the distal tip of the insertion tube 22) may be computed based on the computed distance and orientation between the magnetic sensors 50A, 50B and a model of the catheter 40 which provides the bow of the flexible strips 55 and/or the positions of the electrodes 48 for the computed distance based on the mechanical properties and dimensions of the flexible strips 55.

A method of position and/or direction sensing using external magnetic fields and magnetic coil sensors, such as sensors 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

Processing circuitry 41, typically part of a general-purpose computer, is further connected via a suitable front end and interface circuits 44, to receive signals from body surface-electrodes 49. Processing circuitry 41 is connected to surface-electrodes 49 by wires running through a cable 39 to the chest of patient 28. The catheter 40 includes a connector 47 disposed at the proximal end 29 of the insertion tube 22 for coupling to the processing circuitry 41.

In some embodiments, processing circuitry 41 renders to a display 27, a representation 31 of at least a part of the catheter 40 and a body-part, (e.g., from a mapping process or from a scan (e.g., CT or MRI) of the body-part previously registered with the system 20), based on computed position coordinates of the insertion tube 22 and the flexible strips 55, described in more detail with reference to FIG. 3.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2A:
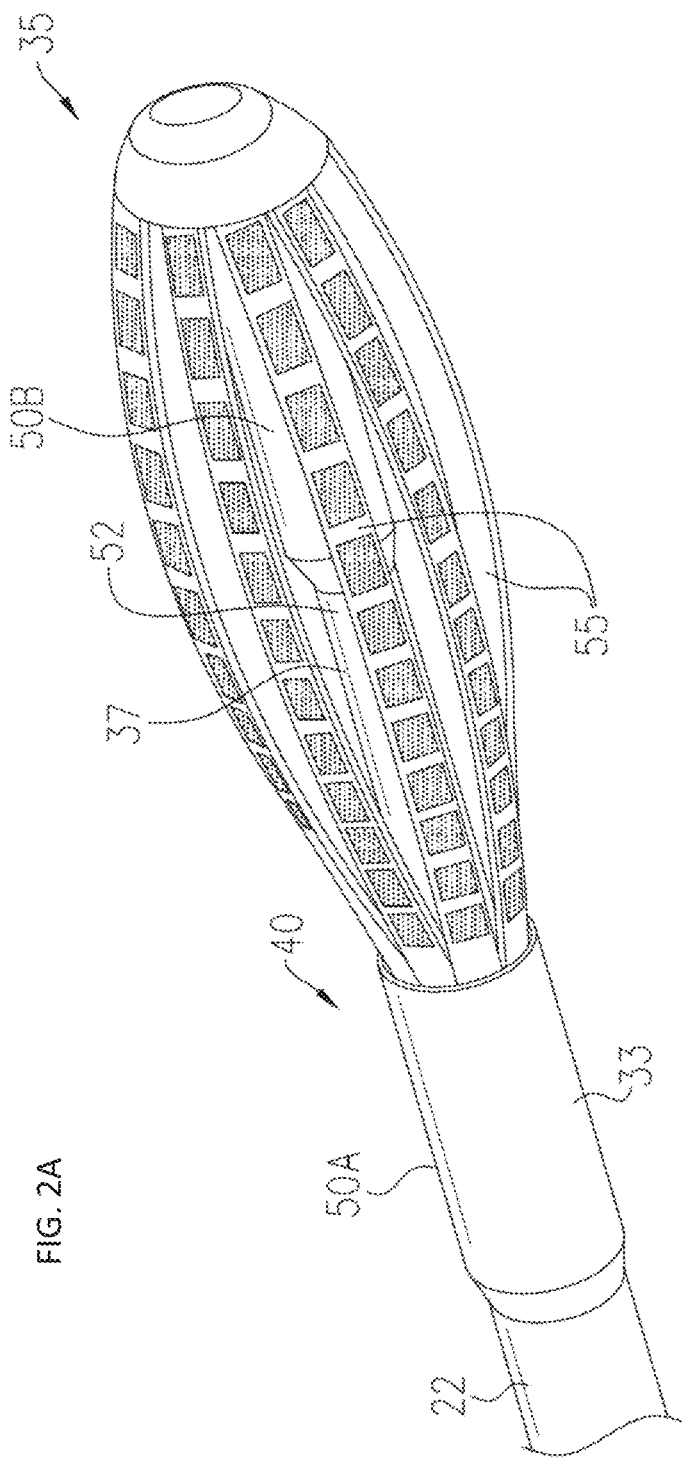
FIG. 2A is a schematic view of a distal end of a basket catheter in a collapsed formation.
Figure 2B:
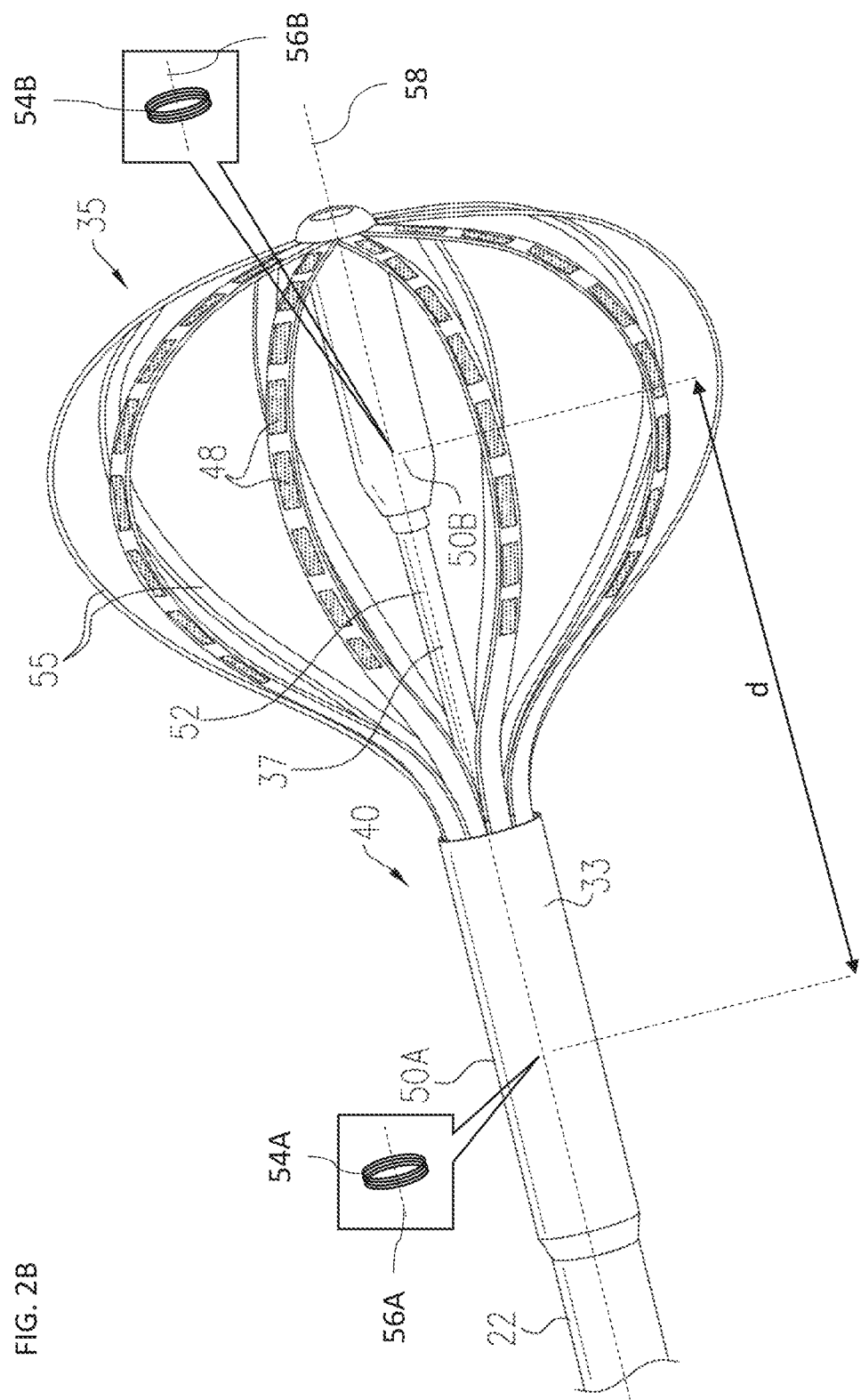
FIG. 2B is a schematic view of the distal end of the basket catheter of FIG. 2A in a deployed formation.

Reference is now made to FIGS. 2A and 2B. FIG. 2A is a schematic view of a distal end 33 of the basket catheter 40 in a collapsed formation. FIG. 2B is a schematic view of the distal end 33 of the basket catheter 40 of FIG. 2A in a deployed formation.

The assembly 35 is typically an expandable distal end assembly (e.g., basket distal end assembly) comprising the flexible strips 55 (only some labeled for the sake of simplicity) disposed circumferentially around a distal portion 52 of the pusher 37 with first ends of the strips 55 connected to the distal end 33 (e.g., the coupling member of the distal end 33) of the insertion tube 22 and second ends of the strips 55 connected to the distal portion 52 (e.g., the coupling member of the distal portion 52) of the pusher 37. The flexible strips 55 are configured to bow radially outward when the pusher 37 is retracted. A plurality of the electrodes 48 (only some labeled for the sake of simplicity) are disposed on each of the flexible strips 55.

The magnetic coil sensor 50A is a coil-based position sensor disposed at the distal end 33 of the insertion tube 22, for example, in the coupling member at the distal end 33. The magnetic coil sensor 50A includes a coil 54A having an axis 56A. The magnetic coil sensor 50B is a coil-based position sensor disposed on the distal portion 52 of the pusher 37, for example, in a coupling member of the distal portion 52, coupling the distal ends of the flexible strips 55 to pusher 37. The magnetic coil sensor 50B includes a coil 54B having an axis 56B. The distal end 33 of the catheter 40 has a longitudinal axis 58. The magnetic coil sensors 50A, 50B are disposed on the distal end 33 with the axis 56A being substantially parallel with the axis 56B. In some embodiments, the axis 56A, the axis 56B, and the longitudinal axis 58 are substantially coaxial.

The pusher 37 is configured to be advanced and retracted through the insertion tube 22. The magnetic field sensors 50A, 50B are configured to move with respect to each other along the longitudinal axis 58 of the catheter 40 as the expandable distal end assembly 35 is expanded and collapsed. When the expandable distal end assembly 35 is collapsed a distance, d, between the magnetic coil sensors 50A, 50B increases, and when the expandable distal end assembly 35 is deployed (i.e. expanded) the distance, d, between the magnetic coil sensors 50A, 50B decreases.

Each sensor 50A, 50B may be a SAS, DAS or TAS. The sensors 50A, 50B may be the same type of sensor, or different types of sensors. If both of the sensors 50A, 50B are single-axis sensors, the catheter 40 generally includes another position sensor to track a roll of the assembly 35.

Figure 3:
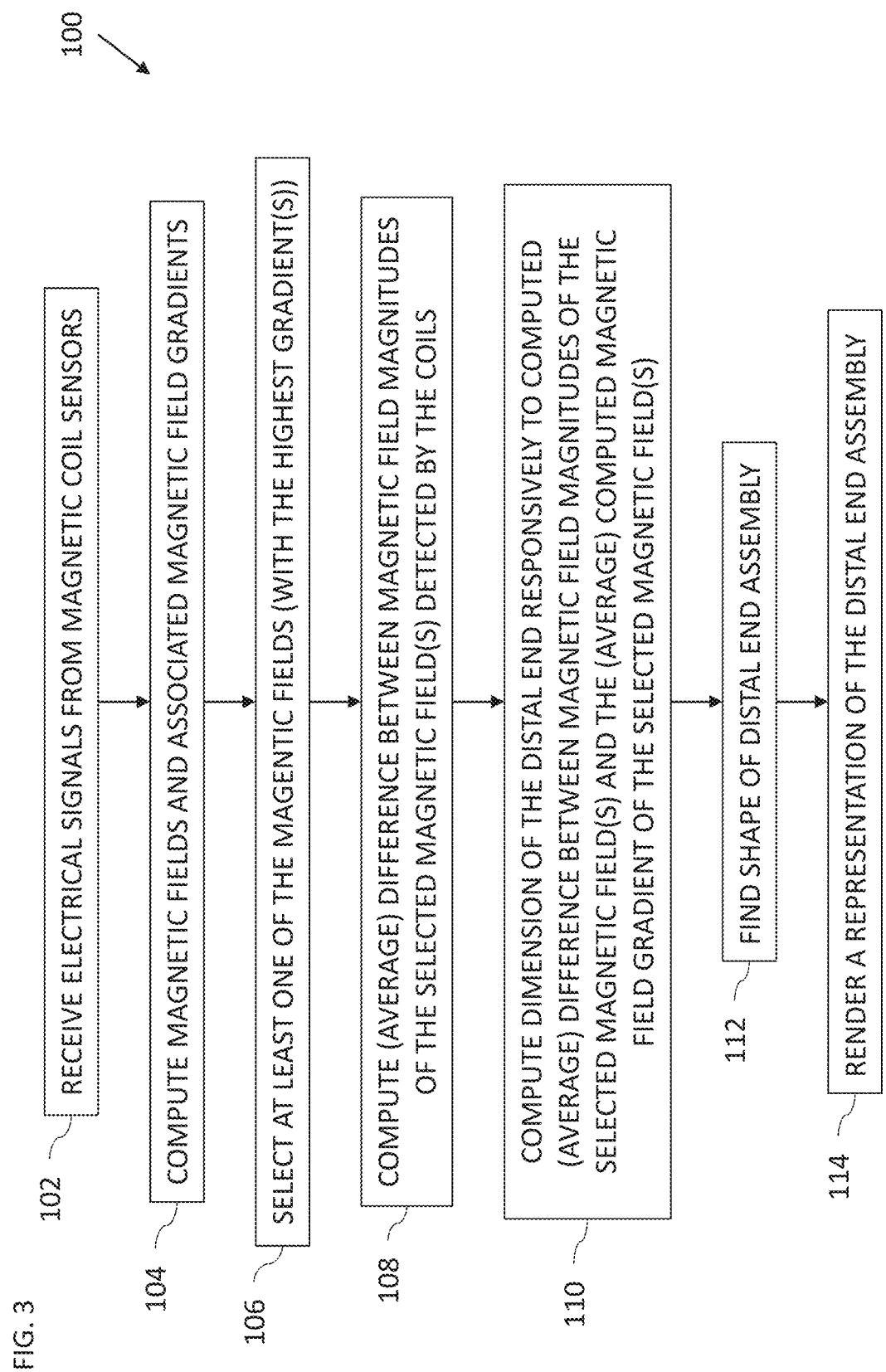
FIG. 3 is a flowchart including steps in a method of operation of the system of FIG. 1.

Reference is now made to FIG. 3, which is a flowchart 100 including steps in a method of operation of the system 20 of FIG. 1. Reference is also made to FIG. 2B.

As previously mentioned, the magnetic coil sensors 50A and 50B are configured to output electrical signals due to the inductive effect of each coil in response the respective magnetic fields. For example, if there are nine magnetic field generator coils 42 generating nine respective different alternating magnetic fields with nine respective different frequencies, the electrical signals output by the magnetic coil sensors 50 will include components of the nine respective different frequency alternating magnetic fields. The magnitude of each of the magnetic fields varies with distance from the respective magnetic field generator coils 42 such that the location of the magnetic coil sensors 50 may be determined from the magnetic fields sensed by the magnetic coil sensors 50. Therefore, the transmitted alternating magnetic fields generate electrical signals in sensors 50A and 50B, such that the electrical signals are indicative of positions and orientation of the magnetic coil sensors 50. The processing circuitry 41 is configured to receive (block 102) the electrical signals from the magnetic coil sensors 50A, 50B.

The processing circuitry 41 is configured to compute (block 104) the magnetic fields detected by the magnetic coil sensor 50A and the magnetic coil sensor 50B, and respective magnetic field gradients (e.g., parallel to the direction of the axes 56A, 56B of the coils 54A, 54B) of respective ones of the magnetic fields detected at the distal end 33. That is, the processing circuitry 41 computes the magnetic field and associated magnetic field gradient from at least one of the electrical signals received by the circuitry 41 from one of more of the magnetic coil sensors 54A and 54B. In some embodiments, an approximate position (location and orientation) of one or more of the magnetic field sensors 50A, 50B may be computed using any suitable method and then based on a known function of the different magnetic fields over three-dimensional (3D) space, the magnetic field gradients at the distal end 33 (e.g., parallel to the direction of the axes 56A, 56B of the coils 54A, 54B) may be found for each of the magnetic fields. The position of the distal end 33 may be computed based on an average position of the magnetic coil sensors 50A, 50B or based on the most accurate sensor of the magnetic coil sensors 50A, 50B. For example, if the sensor 50B is a DAS or TAS, then the location and orientation of sensor 50B may be computed based on all or some of the sensing coils of that sensor.

The processing circuitry 41 is configured to select (block 106) one of magnetic fields having a respective one of the computed magnetic field gradients. In some embodiments, the selected magnetic field has a highest computed magnetic field gradient of the computed magnetic field gradients (i.e. the magnetic field with the highest gradient is selected). The highest magnetic field gradient generally indicates that the selected magnetic field will provide the highest sensitivity in the direction parallel to the axes 56A, 56B of the coils 54A, 54B of the magnetic coil sensors 50A, 50B and will therefore provide the highest accuracy in computing the distance, d, between the sensors 50A, 50B.

In some embodiments, the processing circuitry 41 is configured to select a subset of the magnetic fields (e.g., having the highest magnetic field gradients among the magnetic fields) and compute an average magnetic field gradient of the selected magnetic fields. Therefore, the processing circuitry 41 is configured to select at least one of the magnetic fields having a magnetic field gradient (e.g., an average computed magnetic field gradient) as a function of at least one of the electrical signals received by the circuitry 41 from the coils (which are used to compute the magnetic fields and the magnetic field gradients of the respective magnetic fields). The processing circuitry 41 is configured to compute (block 108) a difference between magnetic field magnitudes of the selected magnetic field (e.g., the magnetic field with the highest gradient) detected by the magnetic coil sensor 50A and the magnetic coil sensor 50B. For example, if the magnetic field magnitude of the selected magnetic field detected by the magnetic coil sensor 50A is equal to B1 and the magnetic field magnitude of the selected magnetic field detected by the magnetic coil sensor 50B is equal to B2, the difference magnetic field magnitudes of the selected magnetic field (e.g., the magnetic field with the highest gradient) detected by the magnetic coil sensor 50A and the magnetic coil sensor 50B is equal to B2 minus B1.

In some embodiments, when a subset of magnetic fields are selected, the processing circuitry 41 is configured to compute a difference (which is an average difference) between magnetic field magnitudes of the selected magnetic fields (e.g., the magnetic field with the highest gradients) detected by the magnetic coil sensor 50A and the magnetic coil sensor 50B. For example, if the average magnetic field magnitude of the selected magnetic fields detected by the magnetic coil sensor 50A is equal to B3 and the average magnetic field magnitude of the selected magnetic fields detected by the magnetic coil sensor 50B is equal to B4, the average difference magnetic field magnitudes of the selected magnetic fields (e.g., the magnetic fields with the highest gradient) detected by the magnetic coil sensor 50A and the magnetic coil sensor 50B is equal to B4 minus B3.

The processing circuitry 41 is configured to compute (block 110) a dimension of the distal end 33, which is a function of the distance d between the magnetic coil sensors 50A and 50B, as a function of the computed difference (e.g., average difference) between the magnetic field magnitudes of the selected magnetic field(s) (e.g., B2 minus B1 or B4 minus B3) and the respective computed magnetic field (average) gradient (e.g., highest computed magnetic field gradient(s)) of the selected magnetic field(s). In some embodiments, the processing circuitry 41 is configured to compute the dimension of the distal end 33 based on the computed (average) difference between the magnetic field magnitudes of the selected magnetic field(s) (e.g., B2 minus B1 or B4 minus B3) divided by the respective computed (average) magnetic field gradient (e.g., highest computed magnetic field gradient(s)) of the selected magnetic field(s). The computed dimension may be the distance between the magnetic coil sensors 50A, 50B. In some embodiments, the computed dimension is a dimension of a shape of the distal end 33 of the catheter, for example, the distance between the proximal and distal points of the distal end assembly 35 or a circumference at the equator of the assembly 35. The processing circuitry 41 is configured to find (block 112) (e.g., by computation or from a lookup table) a shape of the distal end assembly 35 as a derivation from the computed dimension. The processing circuitry 41 is optionally configured to compute a relative orientation between the axes of the sensors 50A and 50B to estimate or derive the shape of the expandable distal end assembly 35 (e.g., a basket shape) based on the relative orientation. The processing circuitry 41 is configured to render (block 114) to the display 27 the representation 31 (FIG. 1) of the distal end assembly 35 as a derivation of the found shape of the distal end assembly 35. One technique for deriving a shape of the expandable distal end assembly 35 based on the distances between magnetic location sensors can be found in U.S. patent application Ser. No. 16/854,538 filed Apr. 21, 2020, which is incorporated by reference with a copy attached in the Appendix.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:
   generator coils configured to generate respective magnetic fields having respective different frequencies in a region of a body part of a living subject;
   a catheter collapsible and expandable between a collapsed formation and a deployed formation along a longitudinal axis of the catheter and being configured to be inserted into the body part of the living subject, and comprising:
   an insertion tube connected to an expandable distal end assembly, and
   magnetic coil sensors configured to output electrical signals in response to the respective magnetic fields, the magnetic coil sensors comprising:
   a first magnetic coil sensor having a first axis, the first magnetic coil sensor being disposed on a distal end of the insertion tube, and
   a second magnetic coil sensor having a second axis, the second magnetic coil sensor being disposed on a pusher tube inside the expandable distal end assembly, the respective axes of the first and second magnetic coil sensors being substantially parallel with each other,
   the first and second magnetic coil sensors being configured to move with respect to each other along the longitudinal axis of the catheter as the expandable distal end assembly is expanded and collapsed such that (i) when the expandable distal end assembly collapses towards the collapsed formation, a distance between the first and second magnetic coil sensors increases, and (ii) when the expandable distal end assembly expands towards the deployed formation, the distance between the first and second magnetic coil sensors decreases; and processing circuitry configured to:
receive the electrical signals from the magnetic coil sensors;
select at least one of the magnetic fields having a magnetic field gradient defined by at least one of the received electrical signals;
compute a difference between magnetic field magnitudes of the at least one selected magnetic field detected by the first magnetic coil sensor and the second magnetic coil sensor based on the received electrical signals; and
compute a dimension of the expandable distal end assembly, which is a function of a distance between the magnetic coil sensors, based on the computed difference between the magnetic field magnitudes of the at least one selected magnetic field and the magnetic field gradient of the at least one selected magnetic field.

2. The medical system according to claim 1, wherein the computed dimension is the distance between the first and second magnetic coil sensors.

3. The medical system according to claim 1, wherein the computed dimension is a dimension of a shape of the expandable distal end assembly of the catheter.

4. The medical system according to claim 1, wherein the processing circuitry is configured to compute the dimension of the expandable distal end assembly as a function of the computed difference between the magnetic field magnitudes of the at least one selected magnetic field divided by the magnetic field gradient of the at least one selected magnetic field.

5. The medical system according to claim 1, wherein:
the at least one selected magnetic field includes one of the magnetic fields having a highest magnetic field gradient of the magnetic fields; and
the processing circuitry is configured to compute the dimension of the expandable distal end assembly as a function of the computed difference between the magnetic field magnitudes of the at least one selected magnetic field and the highest magnetic field gradient.

6. The medical system according to claim 1, wherein:
the first axis and the second axis are substantially parallel in the collapsed formation.

7. The medical system according to claim 6, wherein the first axis, the second axis, and the longitudinal axis are substantially coaxial.

8. The medical system according to claim 6, wherein the expandable distal end assembly is a basket distal end assembly comprising a plurality of flexible strips and electrodes disposed on the flexible strips.

9. The medical system according to claim 6, further comprising a display, and wherein the processing circuitry is configured to:
find a shape of the distal end assembly based on at least the computed dimension; and
render to the display a representation of the distal end assembly based on the found shape of the distal end assembly.

10. The medical system according to claim 9, wherein the computed dimension is the distance between the first and second magnetic coil sensors.

11. The medical system according to claim 1, wherein the processing circuitry is configured to:
compute a relative orientation between the first axis of the first magnetic coil sensor and the second axis of the second magnetic coil sensor; and
estimate a shape of the distal end assembly based on the computed relative orientation.

12. A medical method, comprising:
generating magnetic fields having respective different frequencies in a region of a body part of a living subject;
inserting a catheter into the body part of the living subject, the catheter being collapsible and expandable between a collapsed formation and a deployed formation along a longitudinal axis of the catheter, the catheter comprising:
an insertion tube connected to an expandable distal end assembly; and
a first magnetic coil sensor and a second magnetic coil sensor, each being configured to output electrical signals as a function of respective magnetic fields, the first and second magnetic coil sensors having respective first and second axes substantially parallel with each other, the first magnetic coil sensor being disposed on a distal end of the insertion tube, and the second magnetic coil sensor being disposed on a pusher tube inside the expandable distal end assembly,
the first and second magnetic coil sensors being configured to move with respect to each other along the longitudinal axis of the catheter as the expandable distal end assembly is expanded and collapsed such that (i) when the expandable distal end assembly collapses towards the collapsed formation, a distance between the first and second magnetic coil sensors increases, and (ii) when the expandable distal end assembly expands towards the deployed formation, the distance between the first and second magnetic coil sensors decreases;
detecting respective ones of the magnetic fields with the first and second magnetic coil sensors outputting the electrical signals as the function of the respective magnetic fields;
receiving respective electrical signals from the first and second magnetic coil sensors;
selecting at least one of the magnetic fields having a magnetic field gradient as a function of at least one of the received electrical signals;
computing a difference between magnetic field magnitudes of the at least one selected magnetic field detected by the first magnetic coil sensor and the second magnetic coil sensor as a function of the received electrical signals; and
computing a dimension of the expandable distal end assembly, which is a function of a distance between the first and second magnetic coil sensors, based on the computed difference between the magnetic field magnitudes of the at least one selected magnetic field and the magnetic field gradient of the at least one selected magnetic field.

13. The medical method according to claim 12, wherein the computed dimension is the distance between the first and second magnetic coil sensors.

14. The medical method according to claim 12, wherein the computed dimension is a dimension of a shape of the expandable distal end assembly of the catheter.

15. The medical method according to claim 12, wherein the computing the dimension comprises computing the dimension of the expandable distal end assembly based on the computed difference between the magnetic field magnitudes of the at least one selected magnetic field divided by the magnetic field gradient of the at least one selected magnetic field.

16. The medical method according to claim 12, wherein:
the at least one selected magnetic field includes one of the magnetic fields having a highest magnetic field gradient of the magnetic fields; and
the computing the dimension comprises computing the dimension of the expandable distal end assembly based on the computed difference between the magnetic field magnitudes of the at least one selected magnetic field and the highest magnetic field gradient.

17. The medical method according to claim 12, further comprising moving the first and second magnetic coil sensors with respect to each other along the longitudinal axis of the catheter as the expandable distal end assembly of the catheter is expanded and collapsed between the collapsed formation and the deployed formation, the first and second axes of the first and second magnetic coil sensors being substantially parallel in the collapsed formation.

18. The medical method according to claim 17, wherein the first axis, the second axis, and the longitudinal axis are substantially coaxial.

19. The medical method according to claim 17, further comprising:
finding a shape of the distal end assembly based on at least the computed dimension; and
rendering to a display a representation of the distal end assembly based on the found shape of the distal end assembly.

20. The medical method according to claim 19, wherein the computed dimension is the distance between the first and second magnetic coil sensors.

21. The medical method according to claim 12, further comprising:
computing a relative orientation between the first axis of the first magnetic coil sensor and the second axis of the second magnetic coil sensor; and
estimating a shape of the distal end assembly based on the computed relative orientation.

* * * * *